(12) United States Patent
Anderson et al.

(10) Patent No.: US 6,271,340 B1
(45) Date of Patent: Aug. 7, 2001

(54) METHOD OF CONTROLLING POLYMER MOLECULAR WEIGHT AND STRUCTURE

(75) Inventors: Albert G. Anderson; Alexei Gridnev, both of Wilmington, DE (US); Graeme Moad, Kallista (AU); Ezio Rizzardo, Wheelers Hill (AU); San Hoa Thang, Clayton South (AU)

(73) Assignees: E. I. du Pont de Nemours and Company, Wilmington, DE (US); Commonwealth Scientific & Industrial Research Organization, Victoria (AU)

( * ) Notice: Subject to any disclaimer, the term of this patent is extended or adjusted under 35 U.S.C. 154(b) by 0 days.

(21) Appl. No.: 09/341,282

(22) PCT Filed: Jan. 7, 1998

(86) PCT No.: PCT/US98/00601

§ 371 Date: Nov. 5, 1999

§ 102(e) Date: Nov. 5, 1999

(87) PCT Pub. No.: WO98/30601

PCT Pub. Date: Jul. 16, 1998

Related U.S. Application Data

(60) Provisional application No. 60/034,727, filed on Jan. 10, 1997.

(51) Int. Cl.[7] .................................................. C08G 73/56
(52) U.S. Cl. ......................... 528/423; 528/487; 528/489; 524/839
(58) Field of Search .................................... 528/423, 487, 528/489; 524/839

(56) References Cited

U.S. PATENT DOCUMENTS 4,581,429  4/1986  Solomon et al. ................... 526/220

OTHER PUBLICATIONS

Chem Abstract:*
71: 60404 Stable Free Radicals II. Reactivity of Stable Nitroxide Radicals and N.M.R. Spectra of Reaction Products Murayama et al. 1969 128:13451 Hyshoger Transfer Reactions of Nitroxides in Free Radical Polymerizations Gridnev 1997.*
Georges et al., Taming the Free–Radical Polymerization Process, *Trends Polym. Sci.*, 2, 66–72, 1994.
Hawker, Molecular Weight Control by a "Living" Free-Radical Polymerization Process, *J. Am. Chem. Soc.*, 116, 11185–11186, 1994.
Quirk and Lee, Experimental Criteria for Living Polymerizations, *Polymer International*, 27, 359–367, 1992.
Moad and Rizzardo, Alkoxyamine–Initiated Living Radical Polymerization: Factors Affecting Alkoxyamine Homolysis Rates, *Macromoleculares*, 28, 8722–8728, 1995.

* cited by examiner

*Primary Examiner*—Duc Truong
(74) *Attorney, Agent, or Firm*—James A. Costello; Sudhir G. Deshmukh

(57) ABSTRACT

This invention concerns the preparation of polymers of low polydispersity and/or controlled molecular weight and architecture employing living free radical polymerization initiated by an alkoxyamine initiator or nitroxide plus, optionally a free radical initiator, the polymer produced thereby; selected nitroxide and alkoxyamine initiators; and a process for making the initiators; the polymeric products being useful in protective coatings.

2 Claims, No Drawings

METHOD OF CONTROLLING POLYMER MOLECULAR WEIGHT AND STRUCTURE

This Application is a 371 of PCT/US98/00601 filed Jan. 7, 1998, which claims the benefit of Prov. No. 60/034,727 filed Jan. 10, 1997.

BACKGROUND OF THE INVENTION

This invention concerns the preparation of polymers with low polydispersity and/or controlled molecular weight and architecture by the use of living free radical polymerization initiated by an alkoxyamine or an appropriate nitroxide-initiator combination. It also concerns novel compounds usefull in such polymerizations and methods for their preparation.

Living radical polymerization based on the use of alkoxyamine initiators was invented by Rizzardo et al and is described in U.S. Pat. No. 4,581,429. Recent publications by Georges et al (Trends Polym. Sci., 1994, 2, 66–72), Hawker (J. Am. Chem. Soc., 1994, 116, 11185–11186) and others have described the application of the methodology to the synthesis of narrow polydispersity polystyrenes. The nitroxide component in these latter studies is most often 2,2,6,6-tetramethylpiperidine-1-oxyl (TEMPO) or one of its derivatives. We have now discovered the advantages of nitroxide-mediated living free-radical polymerizations employing imidazoline nitroxides (1) as further defined hereafter:

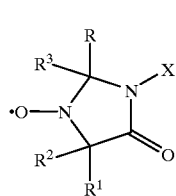

Formula (1)

The characteristics of a living polymerization are discussed by Quirk and Lee (*Polymer International* 27, 359 (1992)) who give the following experimentally observable criteria:

1. Polymerization proceeds until all of the monomer has been consumed. Further addition of monomer results in continued polymerization.
2. The number average molecular weight (or the number average degree of polymerization) is a linear function of conversion.
3. The number of polymer molecules (and active centers) is a constant which is sensibly independent of conversion.
4. The molecular weight can be controlled by the stoichiometry of the reaction.
5. Narrow molecular weight distribution polymers are produced.
6. Block copolymers can be prepared by sequential monomer addition.
7. Chain end-functionalized polymers can be prepared in quantitative yield.

SUMMARY OF THE INVENTION

This invention provides a polymer of the Formula (2) below:

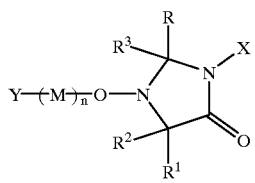

Formula (2)

wherein:
R, $R^1$, $R^2$, $R^3$ are each independently selected from the group consisting of $C_1$ to $C_{18}$ alkyl, substituted $C_1$ to $C_{18}$ alkyl, $C_6$ to $C_{18}$ aryl, $C_6$ to $C_{18}$ substituted aryl; R groups that are in a geminal position with respect to each other can together form a 4–8 membered ring; R groups that are in a cis position with respect to each other can together form a 4–8 membered ring;

X is selected from the group consisting of hydrogen, $C_1$ to $C_{18}$ alkyl, substituted $C_1$ to $C_{18}$ alkyl, $C_6$ to $C_{18}$ aryl, $C_6$ to $C_{18}$ substituted aryl; acyl; X and R can form a 5–8 membered ring; X and $R^3$ can form a 5–8 membered ring;

M is one or more monomer units selected from the group consisting of styrene, substituted styrene, alkyl acrylate, alkyl methacrylate, substituted alkyl acrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene and butadiene;

n is an integer greater than 1;

Y is a residue derived from a species that initiates free radical polymerization or is selected from the group consisting of $C_1$ to $C_{18}$ alkyl, substituted $C_1$ to $C_{18}$ alkyl, $C_1$ to $C_{18}$ alkoxy, substituted C to $C_{18}$ alkoxy, $C_6$ to $C_{18}$ aryl, $C_6$ to $C_{18}$ substituted aryl. $C_6$ to $C_{18}$ aroyloxy, $C_6$ to $C_{18}$ substituted aroyloxy, ($C_1$ to $C_{18}$ alkoxy)carbonyloxy, ($C_6$ to $C_{18}$ aryloxy)carbonyloxy, and sulfate radical anions;

and all substituents are independently selected from the group that consists of epoxy, hydroxy, $C_1$ to $C_{18}$ alkoxy, acyl, acyloxy, alkoxycarbonyl, aryloxycarbonyl, cyano, silyl, halo, and $C_1$ to $C_{18}$ dialkylamino.

The polymers of this invention have low polydispersity which provide improved flow properties in melt or solution. In addition, the presence of the nitroxyl end-group allows the formation of block copolymers by heating the preformed polymer with a different monomer. Alternatively, the nitroxyl end-group can be reduced or chemically modified to give a polymer with a more desirable end-group. The term "polymer(s)" employed herein includes block and graft copolymers and other complex architectures.

Specific monomers or comonomers from which M is derivable include the following:

methyl methacrylate, ethyl methacrylate, propyl methacrylate (all isomers), butyl methacrylate (all isomers), 2-ethylhexyl methacrylate, isobomyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylarnide, N-methylacrylamide, N,N-dimethylacrylamide, N-tert-butylmethacrylamide, N-n-butylmethacrylarnide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers). p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilyLpropyl methacrylate, dibutoxysilyipropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-burylmaleimide, butadiene, isoprene, chloroprene.

This invention provides a process for preparing the polymers of Formula (2) comprising contacting reactant (i) with one or both of reactants (ii) and (iii) wherein:

(i) is at least one monomer M;

(ii) is at least one imidoline nitroxide of the formula

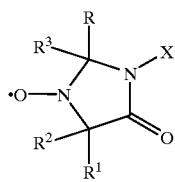

Formula (1)

and a source of free radicals Y•; and (iii) is at least one alkoxyamine selected from the formula

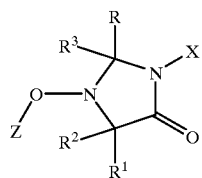

Formula (3)

wherein:

R, $R^1$, $R^2$, $R^3$, X, M and Y are defined above;

Z is a group having at least one carbon atom such that the carbon centered radical Z• is capable of initiating free-radical polymerization of monomer (M); Y and the reaction conditions are selected so that the $Y(M)_n$—O moiety in the compounds of Formula (2) formed from reactants (i) and (ii) undergo facile homolysis; Z and the reaction conditions are selected so that the Z—O moiety and the $Z(M)_n$—O moiety formed by reacting (i) with (iii) undergo facile homolysis; n is an integer of 1 or greater; and Y• can be produced thermally from the monomer (when one of the monomers is styrene or a styrene derivative) or from a free-radical initiator or combination of initiators.

Use of the nitroxides of Formula 1 (or the corresponding alkoxyamines) offers significant advantages over nitroxides previously employed in nitroxide-mediated polymerization: homopolymers, statistical copolymers and block copolymers which have controlled molecular weight, a narrow molecular weight distribution and a defined end-group functionality can be synthesized. The method is also adaptable to the preparation of multi-block and graft and other polymers of more complex architecture. With appropriate selection of the substituents, R, $R^1$, $R^2$, $R^3$, and X, (defined hereafter), the use of the nitroxides (1) offers lower polydispersities and better living character than, for example, TEMPO and derivatives.

Further advantages are that (a) the nitroxides (1) and the derived alkoxyamines are synthesized from readily available precursors by a simple experimental route; (b) they are subject to fewer side reactions (e.g., disproportionation of propagating radical with nitroxide or chain transfer to nitroxide); and (c) they are involatile. This provides an advantage over many of the most commonly used nitroxides such as TEMPO and many of its derivatives, and di-t-butyl nitroxide, which are odorous.

The process can be run continuously or in batch and can be carried out as a solution, emulsion, suspension or bulk polymerization using procedures well known in the art.

If Z is a polymer chain (e.g., $Y(M)_n$—) then the product can be a block copolymer. Block copolymers can also be prepared by the sequential addition of different monomers or monomer combinations. Graft copolymers and polymers of more complex architecture can be prepared from appropriately designed precursors containing multiple nitroxide moieties.

Polymerization reaction conditions include temperatures in the range of about 20° C. to 300° C., preferably between 40° C. to 250° C., and most preferably between 50° C. to 150° C., ambient pressures up to 100 atmospheres and optional solvent(s) compatible with the monomer/polymer systems.

The polymers made by the process in this invention are also characterized by possessing functional end groups which are derived from the moieties Y and/or Z and the nitroxide fragment (1). Such functionality will include hydroxy; carboxylic acid (—COOH) and its esters; cyano; isocyanato; epoxy; halo; amino; and the like.

This invention concerns particular nitroxides of the Formula (1) useful in the polymerization process wherein:

R, $R^1$, $R^2$, $R^3$ are each independently selected from the group consisting of $C_1$ to $C_{18}$ alkyl, substituted $C_1$ to $C_{18}$ alkyl, $C_6$ to $C_{18}$ aryl, $C_6$ to $C_{18}$ substituted aryl; R groups in a geminal position with respect to each other can together form a 4–8 membered ring; and R groups in a cis position with respect to each other can together form a 4–8 membered ring; and X is selected from the group consisting of $C_1$ to $C_{18}$ alky, substituted $C_1$ to $C_{18}$ alkyl, $C_6$ to $C_{18}$ aryl, $C_6$ to $C_{18}$ substituted aryl; acyl; X and R can form a 5–8 membered ring; and X and $R^3$ can form a 5–8 membered ring; with the proviso that R, $R^1$, $R^2$, $R^3$ and X are not all methyl.

Preferred nitroxides selected from the group above are the following:

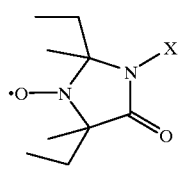

Formula (4)

where X is selected from the group consisting of alkyl, optionally substituted alkyl, benzyl; and

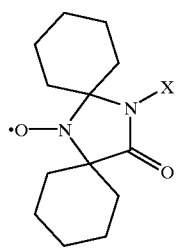

Formula (5)

where X is alkyl of $C_1$ to $C_{18}$.

This invention also concerns novel alkoxyarnines of the Formula (3) wherein:

R, $R^1$, $R^2$, $R^3$ are each independently selected from the group consisting of $C_1$ to $C_{18}$ alkyl, substituted $C_1$ to $C_{18}$ alkyl, $C_6$ to $C_{18}$ aryl, $C_6$ to $C_{18}$ substituted aryl; R groups in a geminal position with respect to each other can together form a 4–8 membered ring, and R groups in a cis position with respect to each other can together form a 4–8 membered ring;

X is selected from the group consisting of hydrogen, $C_1$ to $C_{18}$ alkyl, substituted $C_1$ to $C_{18}$ alkyl, $C_6$ to $C_{18}$ aryl, $C_6$ to $C_{18}$ substituted aryl; acyl; X and R can form a 5–8 membered ring; and X and $R^3$ can form a 5–8 membered ring; and Z is a group having at least one carbon atom and the carbon centered radical Z• is capable of initiating free radical polymerization of the monomer (M).

Suitable Z groups are —C(Me)$_2$Ph, —C(Me)$_2$CN, —C(Me)(CN) CH$_2$CH(Me)$_2$, —C(Me)(CN)(substituted alkyl), —C(Me)$_2$CO$_2$Alkyl, —C(Me)$_2$CO$_2$H, —C(Me)$_2$CH$_2$C(Me)$_3$, —C(Me)$_3$, —C(Me)HPh and Y(M)$_n$—.

This invention also includes a process for making the nitroxides of Formula (1). The process comprises reacting an aminonitrile and a ketone to form a cyanoimine. and reacting said imine with hydrogen sulfide to produce a linear thioamide, and cyclizing said linear thioamide to form a 2,2,5,5,-tetrasubstituted-imidazolidin-4-thione, and converting the cyclic thioamide to the corresponding cyclic amide and then converting the final imidazolidine-4-one to the nitroxide.

In particular, the process for making nitroxides of Formula (1) involves: (i) preparing a colorless aqueous ammonium sulfide solution containing sodium thiocyanate by titrating an aqueous ammonium sulfide solution containing ammonium polysulfide with sodium cyanide under nitrogen; (ii) sequentially adding an aminonitrile and a ketone to the aqueous ammonium sulfide solution under nitrogen; (iii) adding base and then neutralizing; and (iv) oxidizing the reaction product of step (iii) to form the nitroxide.

Alternatively, in process step (ii) aminonitrile can be replaced by a mixture of ketone, ammonium chloride, and sodium or potassium cyanide. In another embodiment of this process, the process is stopped before addition of sodium tungstate and the corresponding cyclic amine/amide is isolated. Process step (ii) can be performed at a temperature of between 20° and 80° C., preferably between 30° and 60° C., and most preferably at 54° C. The base is preferably sodium carbonate or sodium hydroxide, most preferably sodium hydroxide. Any convenient acid can be used for the neutralization, the preferred acid is sulfuric acid. In this process, the concentration of hydrogen peroxide is preferably 20 to 50%, most preferably 30%. The preferred oxidants for the amine to nitroxide transformation are $H_2O_2$/tungstate, dimethyldioxirane, $H_2O_2$/acetic acid.

DETAILS OF THE INVENTION

The most commonly used nitroxides in nitroxide-mediated living free-radical polymerizations have been 2,2,6,6-tetramethylpiperidin-N-oxyl (TEMPO) and derivatives of this compound and di-t-butyl nitroxide (diBuNO).

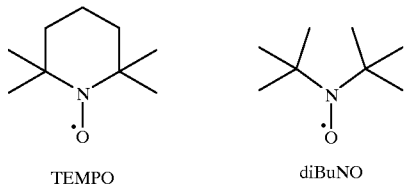

TEMPO        diBuNO

These and other nitroxides/alkoxyamines that are conventionally used in nitroxide-mediated living free-radical polymerizations are inherently of high cost. Substantial cost improvements for the overall process can therefore be achieved by the use of nitroxide (1), a material obtainable from inexpensive precursor by a simple experimental route.

It has been found, that in various polymerizations, the use of certain 2,2,5,5-tetraalkylimidazolin-4-one-1-oxyl derivatives in nitroxide-mediated polymerization offer lower polydispersities for polymers than is obtained with other nitroxides used for this purpose (e.g., TEMPO and derivatives, or diBuNO).

In the context of the present invention, low polydispersity polymers are those with polydispersities that are significantly less than those produced by conventional free radical polymerization. In conventional free radical polymerization, polydispersities (the polydispersity is defined as the ratio of the weight average and number average molecular weights—$\overline{M}_w/\overline{M}_n$) of the polymers formed are typically in the range 1.6–2.0 for low conversions (<10%) and can be substantially greater than this for higher conversions. Polydispersities obtained with the present invention are usually less than 1.5, often less than 1.3 and, with appropriate choice of the nitroxides (1)/alkoxyamines and the reaction conditions, can be less than 1.1. The low polydispersity can be maintained at high conversions.

Polydispersities in nitroxide-mediated polymerization are believed to depend on a number of factors. These include (i) the rate of exchange between active and dormant species which is largely determined by the rate of bond homolysis between N—O and the adjacent moiety for the alkoxyamines involved either as initiator species or formed during the polymerization (for a discussion on this subject see Moad and Rizzardo, *Macromolecules* 1995, 28, 8722-8); and (ii) the significance of various side reactions.

For polymerizations involving nitroxides (1) the rate of bond homolysis between N—O and the adjacent moiety and polydispersities obtained depend on the particular nitroxide or alkoxyamine used and in particular on the substituents R, $R_1$, $R^2$, $R^3$ and X. A preferred group of nitroxides in this context are the N-alkyl-2,2,5,5-tetraalkyimidazolin-4-one-1-oxyl compounds (i.e., (1) X=alkyl, for example, 2,5-bis (spirocyclohexyl)-3-methylimnidazolidin-4-one-1-oxyl (NO-88-Me)) which are seen to offer the lowest polydispersities in styrene polymerizations or copolymerizations. Also preferred within each class (X=alkyl and X=H) are those (1) with more bulky $R-R^3$.

The following are structures of nitroxides described herein:

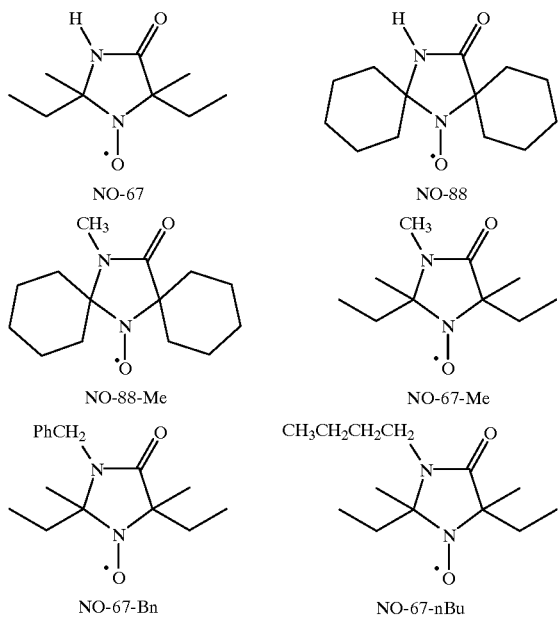

NO-67  NO-88
NO-88-Me  NO-67-Me
NO-67-Bn  NO-67-nBu

It is believed that an important side reaction in nitroxide-mediated polymerization is disproportionation between the nitroxide and the propagating species. It has been found that in methyl methacrylate (MMA) polymerization the use of 2,2,5,5-tetraalkylimidazolin-4-one-1-oxyl derivatives offer low polydispersities and good living character for polymerizations.

While not wishing to be bound by a particular mechanism, these advantages are believed to be in part a consequence of the 5-membered ring imidazoline nitroxides providing a higher combination: disproportionation ratio for the reaction with propagating radicals than 6-membered ring (i.e., TEMPO) or open chain nitroxides (i.e., diBuNO). These pathways are illustrated in Scheme 1 for MMA polymerization. Note that the products of the disproportionation reaction, vinyl terminated macromonomer and hydroxylamine (H—Q) can also react further under polymerization reaction conditions leading to further complications. Clearly, minimization of this side reaction is important to obtaining polymerization with living characteristics.

Scheme 1

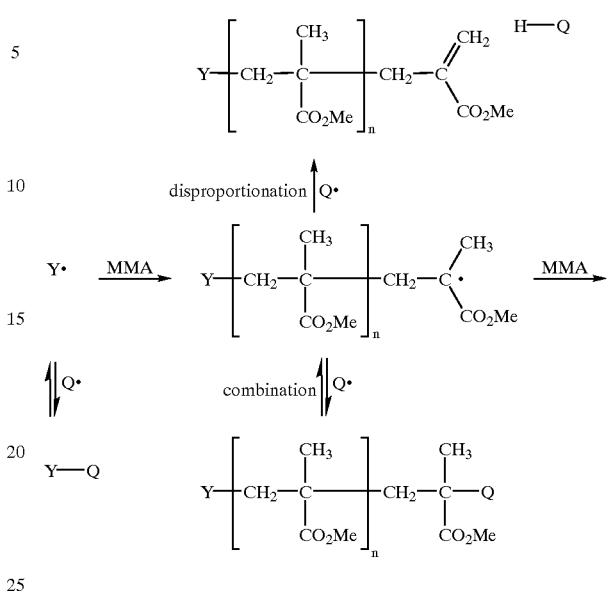

In Scheme 1, Q is a nitroxide.

Similar side reactions have also been shown to occur during nitroxide-mediated styrene polymerization. In styrene polymerization at 90° C., the rate constants for hydrogen transfer from the propagating species to NO-67 and TEMPO relative to the rate constant of propagation have been measured as 0.18 and 0.43 respectively.

In the synthesis of nitroxides of Formula (1), the product nitroxide can be isolated by conventional means, preferably from the reaction mixture by filtrarion or by extraction with an organic solvent that is substantially insoluble in water.

It has been found that the ammonium polysulfide reacts with either aminonitrile or cyanide ion, thereby reducing the amount of cyanide below stoichiometric proportions thus lowering the overall yield. This can be prevented by prior addition of cyanide ion to the point of decolorization of the polysulfide and formation of harmless thiocyanate.

The procedure disclosed herein for synthesis of nitroxides (1, X=H) is as follows:

SCHEME 2

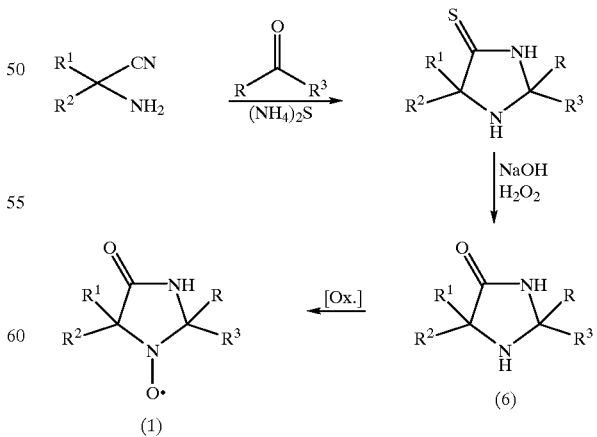

The alkoxyamines of this invention are made from the compounds of Formula (1) by combining them with Z• for example by the procedure of Example 43 and by that described in Macromolecules, 1997, 30, 6445–6450. The alkoxyamines of this invention can be made by a variety of methods such as alkylating the derived hydroxylamines of nitroxides of Formula (1); and alkoxylating the compound of Formula (6) as will be obvious to one skilled in the art.

EXAMPLES

General Experimental Conditions

Monomers were purified (to remove inhibitors) and flash distilled immediately prior to use. Degassing was accomplished by repeated freeze-evacuate-thaw cycles. Once degassing was complete ampoules were flame sealed under vacuum and completely submerged in an oil bath at the specified temperature for the specified times. The percentage conversions were calculated gravimetrically.

The structures of polymers and block copolymers have been verified by application of appropriate chromatographic and spectroscopic methods. Gel permeation chromatography (GPC) has been used to establish the molecular weight and molecular weight distribution (polydispersity) of the polymers. A Waters Associates liquid chromatograph equipped with differential refractometer and $10^6$, $10^5$, $10^4$, $10^3$, 500 and 100 Å Ultrastyragel columns was used. Tetrahydrofuran (flow rate of 1.0 ml/min) was used as eluent. The molecular weights are provided as polystyrene equivalents. The terms $M_n$, $M_w$ and $\overline{M}_w/\overline{M}_n$ are used to indicate the number and weight average molecular weights and the polydispersity respectively. NMR spectroscopy was used to elucidate the structures of polymers and provide evidence for the polymers' end-groups. NMR spectra were obtained on a Bruker (200 MHz) spectrometer and $CDCl_3$ was used as solvent.

Examples 1–5

Styrene Polymerization

These examples show that narrow polydispersity polystyrene can be prepared with NO-88. Polydispersity is initially 1.3 and is reduced to 1.2 over the course of the experiment.
Procedure:

A stock solution contained styrene (9.10 g, 87.5 mmol), benzoyl peroxide (70.7 mg, 0.29 mmol) was prepared. NO-88 (29.1 mg, 0.12 mmol) was added separately to each of 5 ampoules. An aliquot (2 ml) of the stock solution was then added to each ampoule, and the contents of the ampoules were degassed by three freeze-evacuate-thaw cycles. sealed and heated at 130° C. for the designated times. The results are shown in Table 1.

TABLE 1

Bulk Styrene Polymerization in the presence of NO-88 and benzoyl peroxide at 130° C.

| Example | Time/h | $\overline{M}_n$ | $\overline{M}_w/\overline{M}_n$ | $\overline{M}_n$ (calc)[a] | % Conv.[b] |
|---|---|---|---|---|---|
| 1 | 2 | 508 | 1.31 | 235 | 1.5 |
| 2 | 4 | 1626 | 1.27 | 784 | 5.0 |
| 3 | 8 | 4911 | 1.26 | 5334 | 34.0 |
| 4 | 23 | 7061 | 1.21 | 10559 | 67.3 |
| 5 | 72 | 12291 | 1.20 | 14136 | 90.1 |

[a]$\overline{M}_n$ (calc) = [monomer converted]/([BPO] × 2)
[b]% conversion evaluated from $^1$H NMR spectra.

Examples 6–1

MMA Polymerizations

The following section reports results of methyl methacrylate polymerizations in the presence of the azo-initiator, 2,2'-Azobis(2,4-dimethylvaleronitrile) (Vazo®-52) and different nitroxides. The results for NO-67 (Examples 6–9) and NO-88 (Examples 10–12) are shown in Tables 2 and 3 respectively. The effectiveness of these nitroxides is compared with other nitroxides in Table 4. Further sampling after one hour of reaction time shows little or no increase in molecular weight or conversion. The five-membered ring nitroxides (NO-67 and NO-88) gave the most favorable results (narrowest polydispersity). In all cases, the product is believed to be a MMA macromonomer formed by loss of a hydrogen atom from the propagating species to the nitroxide (i.e. reaction by disproportionation rather than combination).
Procedure:

A stock solution was prepared containing MMA (10 ml, 9.36 g) Vazo®-52 (13.43 mg, 0.054 mmol), and NO-67 (14.2 mg, 0.077 mmol). 3 ml of the stock solution was transferred to each of three ampoules which were then degassed through 3 freeze-thaw cycles, sealed, and heated at 90° C. for the indicated times.

TABLE 2

Bulk MMA Polymerization with Vazo ®-52 and NO-67, 90° C.

| Example | time/h | $\overline{M}_n$ | $\overline{M}_w/\overline{M}_n$ | % Conv.[a] | calc. $\overline{M}_n$ |
|---|---|---|---|---|---|
| 6 | 0.5 | 31737 | 1.68 | 24.9 | 30305 |
| 7 | 1 | 38021 | 1.47 | 25.3 | 30730 |
| 8 | 6 | 35709 | 1.57 | 38.2 | 46411 |

[a]% conversion evaluated from mass of polymer obtained.

Procedure:

A stock solution was prepared containing MMA (9 ml, 8.42 g) Vazo®-52 (12.08 mg, 0.049 mmol), and NO-88 (17.16 mg, 0.069 mmol). 3 ml of the stock solution was transferred to each of three ampoules which were then degassed through 3 freeze-thaw cycles, sealed, and heated at 90° C. for the indicated times.

TABLE 3

Bulk MMA Polymerization with Vazo ®-52 and NO-88, 90° C.

| Example | time/h | $\overline{M}_n$ | $\overline{M}_w/\overline{M}_n$ | % Conv.[a] | calc. $\overline{M}_n$ |
|---|---|---|---|---|---|
| 9 | 0.5 | 308 | 1.03 | 0.7 | 866 |
| 10 | 1 | 6472 | 1.44 | 6.4 | 7822 |
| 11 | 6 | 7890 | 1.44 | 5.4 | 6590 |

[a]% conversion evaluated from mass of polymer obtained.

TABLE 4

MMA Polymerizations after 1 hour at 90° C. with VAZO ®-52 and Nitroxide[i]

| Nitroxide | $\overline{M}_n$ | % Conv. | Calculated $\overline{M}_n$ | $\overline{M}_w/\overline{M}_n$ |
|---|---|---|---|---|
| 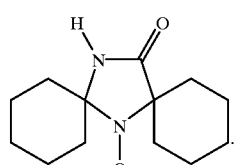 NO-88 | 6472 | 6.4 | 7822 | 1.44 |

TABLE 4-continued

MMA Polymerizations after 1 hour at 90° C. with VAZO ®-52 and Nitroxide[i]

| Nitroxide | $\overline{M}_n$ | % Conv. | Calculated $\overline{M}_n$ | $\overline{M}_w/\overline{M}_n$ |
|---|---|---|---|---|
| NO-67 | 38021 | 24.9 | 30730 | 1.47 |
| TEISO | 18294 | 18.4 | 21528 | 1.71 |
| (isoindoline nitroxide, tetramethyl) | 10515 | 11.2 | 13554 | 2.24 |
| TEMPO | 22073 | 14.3 | 17322 | 3.11 |
| (4-oxo-TEMPO) | 16959 | 17.5 | 21181 | 3.30 |
| DiBuNO | 41904 | 15.4 | 18696 | 3.15 |
| (DiBuNO with ethyl) | 19191 | 17.9 | 21735 | 4.10 |

[i]Reaction conditions similar to those used for experiments described in Tables 2 and 3.

VAZO® is a registered trademark of E. I. du Pont de Nemours and Company. The particular VAZO® compositions referred to herein comprise the following compounds:

VAZO®52 2,2'-azobis(2,4-dimethylvaleronitrile),
VAZO®64 2,2'-azobissisobutyronitrile,
VAZO®67 2,2'-azobis(2-methylbutyronitrile), and
VAZO®88 2,2'-azobis(cyanocyclohexane).

Examples 12 to 27

Styrene Polymerization

A series of styrene polymerizations was conducted in the presence of NO-67, NO-88, and the N-substituted imidazolidinone nitroxides, NO-67-Me, NO-88-Me, NO-67-Bn and NO-67-nBu) and benzoyl peroxide initiator. The polymerization was carried out at 130° C. for a period of times indicated in Table 5 below. Results are summarized in Table 5.

Procedure:

The following six solutions were prepared.
(i) Styrene (5 ml), NO-88 (72.75 mg) and benzoyl peroxide (35.35 mg).
(ii) Styrene (10 ml), NO-88-Me (154.00 mg) and benzoyl peroxide (70.70 mg).
(iii) Styrene (5 ml), NO-67 (56.75 g) and benzoyl peroxide (35.35 mg).
(iv) Styrene (10 ml), NO-67-Me (122.00 mg) and benzoyl peroxide (70.70 mg).
(v) Styrene (5 ml), NO-67-Bn (84.32 mg) and benzoyl peroxide (35.35 mg).
(vi) Styrene (5 ml), NO-67-nBu (73.88 mg) and benzoyl peroxide (35.35 mg).

Aliquots (2 ml) of these solutions were transferred into ampoules and the contents were degassed by three freeze-thaw cycles. The ampoules were then sealed and heated at 130° C. for times indicated in Table 5. The ampoules were cooled, opened and the reaction mixture reduced in vacuo to a residue which was dried to constant weight and analyzed by GPC.

TABLE 5

GPC molecular weight data of polystyrene prepared via polymerizations of styrene with nitroxides and benzoyl peroxide at 130° C.

| Example | Nitroxides | Time/hr | $\overline{M}_n$ | $\overline{M}_w/\overline{M}_n$ | % Conv. |
|---|---|---|---|---|---|
| 12 | NO-88 | 23 | 16047 | 1.23 | 99.0 |
| 13 | NO-88-Me | 2 | 780 | 1.18 | 5.9 |
| 14 | NO-88-Me | 4 | 3115 | 1.13 | 20.9 |
| 15 | NO-88-Me | 8 | 8765 | 1.09 | 56.0 |
| 16 | NO-88-Me | 18 | 16271 | 1.09 | 96.0 |
| 17 | NO-88-Me | 23 | 16300 | 1.09 | 99.0 |
| 18 | NO-67 | 23 | 16043 | 1.49 | 99.0 |
| 19 | NO-67-Me | 2 | 502 | 1.36 | 5.0 |
| 20 | NO-67-Me | 4 | 1380 | 1.29 | 9.9 |
| 21 | NO-67-Me | 8 | 2499 | 1.34 | 22.4 |
| 22 | NO-67-Me | 18 | 4693 | 1.29 | 49.4 |
| 23 | NO-67-Me | 23 | 8075 | 1.24 | 60.0 |
| 24 | NO-67-Bn | 4 | 1402 | 1.23 | 9.1 |
| 25 | NO-67-Bn | 18 | 5102 | 1.28 | 47.4 |
| 26 | NO-67-nBu | 4 | 1430 | 1.22 | 8.8 |
| 27 | NO-67-nBu | 18 | 6013 | 1.25 | 53.0 |

The proton-NMR spectrum of a polystyrene sample ($\overline{M}_n$ 3115) of Example 14 had signal at δ 2.90 ppm clearly indicating the presence of the N-methyl of the 2,5-bis(spirocyclohexyl)-3-methylimidazolidin-4-one-1-oxyl (NO-88-Me) end group.

Examples 28–31

Acrylate Polymerization

Polymerization of tert-butyl acrylate was carried out in sealed tubes at using the alkoxyamine, 1-(2-tert-butoxy-1- phenylethoxy)-2.5-rocyclohexyl)-3-methylimidazolidin-4-one as initiator-terminator. This example demonstrates the acrylate polymers with low polydispersity (1.3–1.4) can be obtained.

Two set of experiments were conducted:

(i) A stock solution of the alkoxyamine (71.3 mg), tert-butyl acrylate (1.0 ml) in benzene (4.0 ml) was prepared. Aliquots (2.0 ml) were transferred into ampoules (×2) and the contents were degassed by three freeze-thaw cycles. The ampoules were then sealed and heated at 120° C. for 24 hours and 49 hours respectively. Results are shown in Table 6 below.

TABLE 6 tert-Butyl acrylate polymerizations in the presence of alkoxyamine in benzene at 120° C.

| Example | Time (hr) | $\overline{M}_n$ | $\overline{M}_w/\overline{M}_n$ | % Conv. |
|---|---|---|---|---|
| 28 | 24 | 1525 | 1.39 | 28.0 |
| 29 | 49 | 1830 | 1.32 | 34.4 |

The proton-NMR spectrum of a sample of poly(tert-butyl acrylate) of Example 28 ($\overline{M}_n$ 1525) had signals at δ 8 7.10 ppm indicating the presence of phenyl group (cf. δ 3 7.30 ppm for the original alkoxyamine used) and d 2.90 ppm indicating the presence of the N-methyl group of the NO-88-Me.

(ii) A stock solution of alkoxyamine (71.3 mg), tert-butyl acrylate (5.0 ml) was prepared. Aliquots (2.0 ml) were transferred into ampoules (×2) and the contents were degassed by three freeze-thaw cycles. The ampoules were then sealed and heated at 120° C. for 24 hours and 49 hours respectively. Results are shown in Table 7 below.

TABLE 7

Bulktert-Butyl acrylate polymerizations in the presence of alkoxyamine at 120° C.

| Example | Time (hr) | $\overline{M}_n$ | $\overline{M}_w/\overline{M}_n$ | % Conv. |
|---|---|---|---|---|
| 30 | 24 | 8272 | 1.51 | 28.6 |
| 31 | 49 | 9005 | 1.41 | 39.8 |

Examples 32–33

Block Copolymer Syntheses

The following two examples [polystyrene-block-poly(4-methylstyrene) and polystyrene-block-poly(n-butyl acrylate)] demonstrate the synthesis of block copolymers. The samples were prepared by heating a narrow polydispersity polystyrene (derived from NO-88-Me)($\overline{M}_n$ 8765, $\overline{M}_w/\overline{M}_n$ 1.09; see Table 5, Example 15) with 4-methylstyrene and n-butyl acrylate respectively. Results are excellent in both cases and give low polydispersity block copolymers.

Example 32

Polystyrene-block-poly(4-methylstyrene)

To an ampoule, a sample of poly styrene (250 mg) $\overline{M}_n$ 8765, $\overline{M}_w/\overline{M}_n$ 1.09; Example 15) was dissolved in 1 ml of 4-methylstyrene (freshly distilled). The contents of the ampoule was degassed and sealed under vacuum. Subsequently, the mixture was polymerized at 130° C. for 18 hours and gave a narrow polydispersity polystyrene-block-poly(4-methylstyrene) (0.85g, 95% conversion), $\overline{M}_n$ 36872, $\overline{M}_w/\overline{M}_n$ 1.14.

Example 33

Polystyrene-block-poly(n-butyl acrylate)

To an ampoule, a sample of polystyrene (250 mg) ($\overline{M}_n$ 8765, $\overline{M}_w/\overline{M}_n$ 1.09; Example 15) was dissolved in 1 ml of n-butyl acrylate (freshly distilled). The contents of the ampoule was degassed and sealed under vacuum. Subsequently, the mixture was polymerized at 130° C. for 18 hours and gave a narrow polydispersity polystyrene-block-poly(n-butyl acrylate) (0.608 g, 68% conversion), $\overline{M}_n$ 21526, $\overline{M}_w/\overline{M}_n$ 1.29.

Examples 34–36

Statistical Copolymer Syntheses

A series of styrene/acrylonitrile (62:38 molar ratio; the azotropic composition) copolymerizations in the presence of N-substituted imidazolidinone nitroxides NO-88-Me, NO-67-Me and NO-67-Bn. The experiments were conducted thermally at 130° C. for 18 hours. Results are summarized in Table 8.

Procedure:

A stock solution (I) of fresh ly distilled styrene (7.27 g) and acrylonitle (2.27 g) was prepared. Each ampoule contains stock solution (2 g) and nitroxide ($1.23 \times 10^{-4}$ mol). The content was degassed, sealed and heated at 130° C. for 18 hours.

TABLE 8

GPC data of styrene/acrylonitrile copolymers prepared thermally at 130° C. with different nitroxides.

| Example | Nitroxide | $\overline{M}_n$ | $\overline{M}_w/\overline{M}_n$ | % Conv. |
|---|---|---|---|---|
| 34 | NO-88-Me | 23098 | 1.16 | >95.0 |
| 35 | NO-67-Me | 17035 | 1.34 | 84.0 |
| 36 | NO-67-Bn | 17605 | 1.35 | 89.0 |

Examples 37–42

Syntheses of Nitroxides of Formula (1)

The following Examples 37–38 illustrate the novel process for synthesis of nitroxides (1, where X=H).

Example 37

Preparation of 2,5-diethyl-2,5-dimethylimidazolidin-4-one-1-oxyl (NO-67) Preparation of 2,5-diethyl-2,5-dimethylimidazolidin-4-thione A 1 liter 4-necked round-bottomed flask equipped with a mechanical stirrer, thermocouple thermometer, nitrogen bubbler, bleach-filled scrubber, and reflux condenser was charged with 17.4 g ammonium chloride (0.32 mol), 35.9 g AN-67 (0.3 mol, 87% 2-amino-2-methylpropionitrile in water, $^1$H NMR (ppm) of freshly distilled AN-67 in $D_2O$: 1.03 (t, 3H), 2.45 (s, 3H), 1.75 (q, 2H), 23.1 g 2-butanone (0.32 mol), and 132.9 g of 20% ammonium sulfide solution (0.39 mol). As the solution was heated to 50° C., a slight exotherm occurred that increased the temperature to 65° C. and some ammonium hydrosulfide sublimed into the condenser. After 20 minutes, the temperature declined to 55° C. and was held there for 18 hours. An oily liquid layer forms on top of the aqueous solution during the first 5 minutes. The yellow polysulfide color is discharged in the first minute; this is caused by reaction of cyanide ion with sulfur to give colorless thiocyanate ion and a decrease in yield. The next day, the solution was cooled to −15° C., 25 g of NaCl added to salt out the thione, and filtered cold to give 39 g of product. The mother liquor was treated with 10 g of $K_2CO_3$ to precipitate an additional 5 g of product. $K_2CO_3$ is more effective at salting out thiones, amides, and nitroxides than NaCl. The solids were combined to give 44 g (80% yield) of thione after 2 days of air drying, mp. 58–64° C. IR (nujol) 1540 cm-1; $^1$H NMR ppm ($D_2O$) 0.96 (overlapping t, 12H, $CH_3$ on 4 ethyls), 1.39,1.40,1.42,1.43 (4 singlets, total of 12H, $CH_3$ for four isomers, i.e., 2 cis-trans pairs), 1.75 (m, 8H, 4 $CH_2$ groups).

| combustion analysis: | calcd. for $C_9H_{18}N_2S.0.1(H_2O)$ | obs. |
|---|---|---|
| C | 57.46 | 57.90 |
| H | 9.75 | 9.24 |
| N | 14.89 | 14.94 |
| S | 17.05 | 16.68 |

The thione can be purified by column chromatography on silica gel using hexane to elute an odorous fraction before the thione. The effect of variation of temperature and concentration of the reactants on yield and reaction rate was examined in a sealed NMR tube using $D_2O$ as a solvent and sodium tosylate as an internal standard. What was observed was a smooth decrease in concentration of starting materials and smooth increase in concentration of product. The reaction time can be reduced from 16 hours at 50° C. to 6 hours at 80° C. The compound, 2-methyl-2-aminobutyrothioamide, was not observed indicating that this alicyclic intermediate reacts with MEK in a fast step to yield the cyclic product.

Preparation of 2,5-diethy-2,5-dimethylimidazolidin-4-one

A 5 liter 4-necked round-bottomed flask equipped with a mechanical stirrer and thermocouple thermometer was charged with 250 ml water and 43.3 g (0.232 mol) of 2,5-diethyl-2,5-dimethylimidazolidin-4-thione. In order to make the thione dissolve, 1.8 g NaOH was added. The solution was cooled to 0–2° C. with a dry ice-acetone bath. The flask was fitted with two additional funels. Simultaneously, a solution of 16.7 g NaOH in 100 ml water (total of 18.5 g or 0.464 mol of NaOH used) was added through one of the funnels and 105 ml (0.928 mol) of 30% $H_2O_2$ was added through the other funnel. The reaction mixture was stirred rapidly and required extensive cooling during the addition. The 5 liter flask was used to provide a large surface area for efficient cooling of the exothermic reaction. The heat of reaction was 269.2 Kcal/mol; 124. The addition was completed in 2 hours; the mixture was stirred an additional half hour. At the end of this time, TLC indicated that no thione remained. Then, 27.9 g of $NaHSO_3$, (0.172 mol) was added to quench excess peroxide; this reaction is also somewhat exothermic (temperature increases from 26 to 43° C.). The reaction mixture was transferred to a 2 liter round-bottomed flask and the solvent removed with a rotary evaporator (aspirator pressure) to give a white residue. The residue was extracted with 850 ml of boiling ethanol. Then, 50 ml of toluene was added to the solution and 130 ml of water/ethanol/toluene azeotrope distilled to remove any remaining water. The solution was cooled and filtered to remove a small amount (~1 g) of $Na2SO_4$ and then the ethanol was removed on the rotary evaporator to give a syrup that crystallized on cooling to room temperature. The yield was 37.5 g (95%) mp 58–64° C. IR (nujol) 1705, 1659 cm-1. $^1$H NMR ($CDCl_3+D_2O$) ppm (combination of equal amounts of 2 sets of cis-trans pairs) 0.95–0.98 (m, 12H, $CH_3$ on 4 ethyls), 1.27, 1.31, 1.34, 1.38 (4 s, total 12H, 4 $CH_3$), 1.50–1.70 (m, 8H, $CH_2$ on 4 ethyls). The singlets at 1.34 and 1.38 collapse to a singlet in $D_2O$ but now integrate 6H.

| combustion analysis: | calcd. for $C_9H_{18}N_2O$ | obs. |
|---|---|---|
| C | 63.49 | 63.07 |
| H | 10.66 | 10.01 |
| N | 16.45 | 16.23 |
| O | 9.40 | 9.49 |

Preparation of 2,5-diethl-2,5-dimethylimidazolidin-4-one-1-oxyl

A one liter polymer jar equipped with a mechanical stirrer, bleach filled odor trap, heating mantel, reflux condenser, and thermocouple thermometer was charged with 153.3 g (0.45 mol) 20% ammonium sulfide solution. To this solution was added 1.47 g (0.03 mol) NaCN to react with the ammonium polysulfide impurity in the ammonium sulfide solution. Then, 35.9 g AN-67 (0.3 mol) and 21.7 g 2-butanone (0.3 mol) was added. The solution was stirred and heated under nitrogen at 55° C. for 18 hours; some ammonia was evolved. Two liquid layers form; the lower layer is thioamide. The volume of the reaction mixture is now 200 ml. The mixture was cooled to room temperature and a solution of 36 g NaOH (0.9 mol) in 100 ml water was added. The solution was cooled to 0° C. and 306 g (2.7 mol) 30% $H_2O_2$ added dropwise with stirring and cooling at 4–10° C. The addition took 65 minutes. After stirring for one hour, the solution was brought to pH=7 by addition of a solution of 58 g concentrated $H_2SO_4$ and 56 g of water at 13° C. Then, 68 g (0.6 mol) of 30% $H_2O_2$ was added. No exotherm was noted at this time. To this was added 5.0 g $Na_2WO_4.2H_2O$. The total reaction volume is 763 ml. An initial greenish-yellow color (pertungstate ion) is replaced by a deeper yellow color (nitroxide). The temperature of the mixture climbs from 13 to 31° C. over 3½ hours The next day, the solution was filtered to give 27.5 g (40% yield) of nitroxide, mp 117–122° C. It was subsequently found that ⅓ of the AN-67 is destroyed by hydrolysis and irreversible reaction with sulfur to form thiocyanate ion. If this is taken into account, the yield is 82%; each step is about 93%. The solubility in NMP is at least 1:1. IR (nujol) 1720, 1675 cm-1; (toluene solution) 1713.3 cm-1. The nitroxide displays a triplet in the ESR. Aliquots of reaction rnixture were withdrawn at selected times and diluted with a known amount of xylene. The integrated intensity of the ESR triplet was plotted as a finction of time when the concentration of peroxide was doubled or the concentration of tungstate ion was increased to three. The data were fitted to parabolas. The initial slopes of the lines are obtained by differentiating the empirically fitted curves to determine the slope of the line and solving the equation so obtained at x=0; the rate law at 24° C. was found to be $K=k[H_2O_2]^{0.5+0.1}[WO_4^=]^{1.0+0.1}$

| combustion analysis: | calcd. for $C_9H_{17}N_2O_2.0.03(CH_2Cl_2)$ | obs. |
|---|---|---|
| C | 57.75 | 57.71 |
| H | 9.16 | 8.82 |
| N | 14.92 | 15.21 |
| O | 17.04 | 17.28 |

Examule 38

Preparation of 2,5-bis(spirocyclohexyl)imidazolidin-4-one-1-oxyl (NO-88)

Preparation of 2,5-bis(spirocyclohexyl)imidazolidin-4-thione.

A 2 liter 4-necked round-bottomed flask equipped with a mechanical stirrer, heating mantel, reflux condenser, thermocouple thermometer, nitrogen bubbler and exit tube connected to a bleach filled odor trap was charged with 132.9 g (0.39 mol) of 20% ammonium sulfide solution followed by 0.5 g NaCN to decolorize the polysulfide impurity in the ammonium sulfide solution. Under a positive nitrogen flow, 16.1 g (0.3 mol) of ammonium chloride and 14.7 g (0.3 mol) of NaCN was added. The temperature of the solution dropped to 8° C. Then, 58.9 g (0.6 mol) of cyclohexanone that had previously been deoxygenated by bubbling nitrogen through it for 10 minutes was added dropwise while stirring during 25 minutes. The temperature rose to 30° C. The temperature of the solution was increased to 47° C., at which point external heating was stopped and the reaction spontaneously allowed to exotherm to 63° C. The temperature was then maintained at 55° C. After 1 hour, 1.0 g NaCN was added and a mild exotherm to 63° C. followed by a return to 55° C. was noted. An additional 1.0 g NaCN was added 30 minutes later; this caused only a mild exotherm to 58° C. The temperature was held at 55° C. overnight. A sample of the resulting slurry was then withdrawn and divided into two parts. One part was dissolved in acetone, and checked by TLC (9:1 $CH_2Cl_2$:acetone); two species were present. The other part was filtered to give white crystals, mp 225–230° C. The precipitate was filtered in place with a filter stick to avoid handling the odorous mixture. The insoluble precipitate was thione; the other impurity was cyclohexanone, which remained in the filtrate. The thione was washed by adding 300 ml of water to the flaskr stirring, and then removing the water through the filter stick. IR (nujol) 1520 cm-1.

Preparation of 2,5-bis(spirocyclohexyl)imidazolidin-4-one

To the wet crystalline residue obtained above was added in the same flask 24 g (0.6 mol) of NaOH dissolved in 300 ml of water. The crystals failed to dissolve; the crystals were finally dissolved by addition of 485 ml of methanol. The solution does not show the characteristic exotherm upon addition of 30% hydrogen peroxide at 0–5° C. The temperature of the solution was increased to 40° C.; at this temperature addition of peroxide is exothermic. After adding 147 g (4×0.32 mol) of 30% peroxide, the solution temperature was held at 55° C. for 30 minutes and then stirred at room temperature overnight; by TLC, the mixture consisted of amide and thione. The mixture was filtered and the precipitate washed with 3×100 ml of water. To the filtrate was added 57 g of peroxide [total peroxide used=204 g (1.8 mol)] and the solution was warmed to 40° C. A slight exotherm to 46° C. occurred. To aid the oxidation, 1 g of $Na_2WO_4.2H_2O$ was added. After 15 minutes, a white precipitate began to deposit. The mixture was allowed to stir at room temperature for 18 hours and then filtered. By IR, both precipitates were identical and were combined and air dried, mp 216–220° C., 58.5 g (88% yield based on cyclohexanone). IR (nujol) 1690 cm-1.

Preparation of 2,5-bis(spirocyclohexyl)imidazolidin-4-one-1-oxyl

An acetone solution of 260 ml of 0.08M dimethyldioxirane (0.0208 mol), prepared as above, was treated with 2.3 g of 2,5-bis(spirocyclohexyl)imidazolidin-4-one dissolved in 75 ml of chloroform (previously freed of ethanol preservative by washing with 2×20 ml water and drying over magnesium sulfate) and allowed to react at room temperature overnight. The preparation was repeated using 1.7 g of amide and 270 ml of 0.0721M dimethyldioxirane solution. Removal of the ethanol preservative is necessary to prevent the ethanol from being oxidized to acetaldehyde by the dimethyldioxirane/nitroxide system. The solvent was removed on the rotary evaporator, the residue (4.2 g) dissolved in 400 ml hot benzene, filtered to remove a trace of insoluble material, the filtrate reduced to 100 ml, rewarmed to bring all the crystals into solution, and allowed to crystallize overnight at room temperature. The yellow crystals were collected by filtration and dried in an oven at 75° C. for 10 hours to give 2.4 g of nitroxide, mp 178–183° C. IR (nujol) 1707 cm-1.

| combustion analysis: | calcd. for $C_{13}H_{21}N_2O_2$ | obs. |
|---|---|---|
| C | 65.79 | 65.67 |
| H | 8.92 | 8.84 |
| N | 11.80 | 11.71 |
| O | 13.48 | 13.31 |

Examples 39–42

Synthesis of N-substituted Imidazolidinone Nitroxides

The following Examples 39–42 illustrate the process for synthesis of novel nitroxides (1, X=Alkyl).

The novel N-substituted imidazolidinone nitroxides were prepared according to the following general procedure.

A suspension of imidazolidinone nitroxide (5.5 mmol NO-67 or 1.69 mmol NO-88) and sodium hydride (1.33 molar eq., 80% dispersion in oil) was allowed to stir under an atmosphere of nitrogen in acetonitrile solvent (20 ml for NO-67 or 10 ml for NO-88) at room temperature for 15 minutes, and then added the required amount of an alkyl halide (1.20 molar equivalents). After workup and purification by column chromatography, the corresponding new N-substituted imidazolidinone nitroxide was generally obtained in good to excellent yield (45–93%).

Example 39

Preparation of 2,5-Bis(spirocyclohexyl)-3-methylimidazolidin-4-one-1-oxyl (NO-88-Me)

The title compound, NO-88-Me was isolated as a yellow solid after column chromatography (Kieselgel-60, 70–230 mesh, ethyl acetateln-hexane 1:4 as eluent) (89.7% yield). Melting point, 103–105° C. MS (CI): 252 (M+1, 100%), 251 (M+, 30.7), 237 (87.6), 236 (12.3), 235 (29.3), 222 (24.5), 221 (40.6), 196 (18.7), 193 (10.5), 142 (24.7), 140 (53.9), 112 (16.0) and 99 (23.5).

Example 40

Preparation of 2,5-Diethyl-2,3,5-trimethylimidazolidin-4-one-1-oxyl (NO-67-Me)

The title compound, NO-67-Me was isolated (45.6% yield) after column chromatography (Kieselgel-60, 70–230 mesh, ethyl acetate/n-hexane 1:3 as eluent) as a yellow liquid. MS (CI): 200 (M+1, 43.0%), 199 (M+, 16.0), 186 (23.5), 185 (40.0), 171 (58.0), 170 (34.0), 155 (23.0), 149 (20.2), 141 (11.6), 140 (15.6), 128 (10.0), 126 (16.1), 116 (13.7), 112 (14.4), 111 (12.7), 100 (12.2), 73 (52.0).

Example 41

Preparation of 2,5Diethyl-2,5-dimethyl-3-benzylimidazolidin-4-one-1-oxyl (NO-67-Bn)

The title compound, NO-67-Bn was isolated (93.0% yield) after column chromatography (Kieselgel-60, 70–230 mesh, ethyl acetate/n-hexane 1:5 as eluent) as a yellow solid. Melting point, 64–65° C. MS (CI): 276 (M+1, 56.7%), 275 (M⁺, 22.0), 262 (22.0) 261 (100.0), 247 (62.6), 245 (M-NO, 26.0), 231 (86.0), 218 (5.3), 190 (12.3), 170 (15.0), 162 (24.6), 126 (20.1), 102 (4.0), 91 (21.5) and 72 (4.0).

Example 42

Preparation of 2,5-Diethyl-2,5-dimethyl-3-n-butylimidazolidin-4-one-1-oxyl (NO-67-nBu)

The title compound, NO-67-nBu was isolated (87.0% yield) after column chromatography (Kieselgel-60, 70–230 mesh, ethyl acetate/n-hexane 1:9 as eluent) as a yellow liquid. MS (CI): 242 (M+1, 74.0%), 241 (M⁺, 38.3), 227 (100.0), 213 (86.7), 211 (45.0), 198 (12.0), 197 (88.0), 184 (M-nBu, 7.6), 170 (27.0), 156 (16.3), 128 (27.0), 126 (30.0), 116 (4.3), 98 (8.0) and 72 (7.6).

Example 43

Synthesis of Alkoxyamine of Formula (3)
Preparation of 1-(2-tert-butoxy-1-phenylethoxy)-2,5-bis(spirocyclohexyl)-3-methylimidazolidin-4-one The title alkoxyamine, 1-(2-tert-butoxy-1-phenylethoxy)-2,5-bis(spirocyclohexyl)-3-methylimidazolidin-4-one was prepared by treating 1-(2-tert-butoxy-1-phenylethoxy)-2,5-bis(spirocyclohexyl)-imidazolidin-4-one alkoxyamine (m.p. 244–247° C., obtained from the reaction of di-tert-butyl peroxyoxalate, styrene and nitroxide NO-88) with excess methyl iodide in the presence of sodium hydride in dimethyl sulfoxide solvent (Scheme 3). The product was isolated as a white solid in 93% yield, m.p. 129–131° C. (aq. MeOM). The alkoxyamine product has improved solubility versus its non-methylated alkoxyamine and is readily soluble in common organic solvents such as ethyl acetate, chloroform, acetone, hot methanol. ¹H-NMR (CDCl₃) δ (ppm) 0.40–2.60 (m, 20OH, cyclohexyl-CH₂), 1.10 (s, 9H, tert-butyl-CH₃), 2.90 (s, 3H, N-CH₃), 3.30 (dd, 1H, (CH₃)₃COCH), 3.66 (dd, 1H,(CH₃)₃COCH), 4.69 (dd, 1H, CH(Ph)ON) and 7.25 (br s, 5H, phenyl-H).

Scheme 3

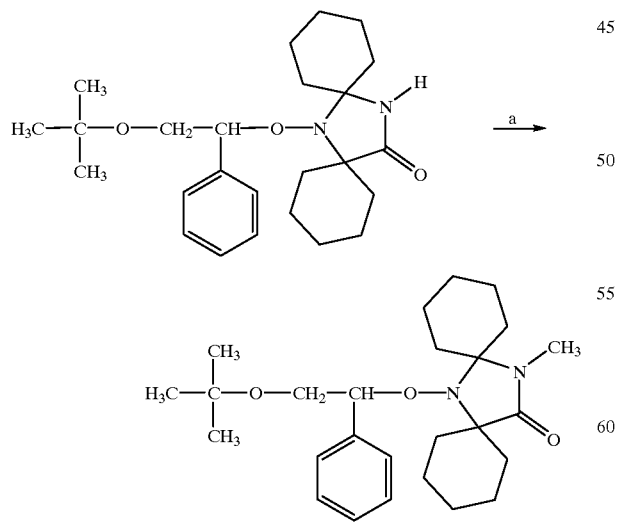

a) NaH/DMSO, excess methyl iodide, at room temperature.

What is claimed is:
1. A polymer of the formula:

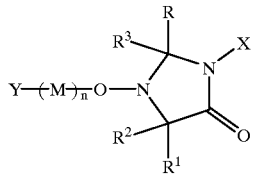

Formula (2)

wherein:

R, R¹, R², R³ are each independently selected from the group consisting of C₁ to C₁₈ alky, substituted C₁ to C₁₈ alkyl, C₆ to C₁₈ aryl, C₆ to C₁₈ substituted aryl; R groups in a geminal position with respect to each other can together form a 4–8 membered ring; and R groups in a cis position with respect to each other can together form a 4–8 membered ring;

X is selected from the group consisting of hydrogen, C₁ to C₁₈ alkyl, substituted C₁ to C₁₈ alkyl, C₆ to C₁₈ aryl, C₆ to C₁₈ substituted aryl; acyl; X and R can form a 5–8 membered ring; and X and R³ can form a 5–8 membered ring;

M is one or more monomer units selected from the group consisting of styrene, substituted styrene, alkyl acrylate, alkyl methacrylate, substituted alkyl acrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene and butadiene;

n is an integer greater than 1;

Y is a residue derived from a species that initiates free radical polymerization or is selected from the group consisting of C₁ to C₁₈ alkyl, substituted C₁ to C₁₈ alkyl, C₁ to C₁₈ alkoxy, substituted C₁ to C₁₈ alkoxy, C₆ to C₁₈ aryl, C₆ to C₁₈ substituted aryl, C₆ to C₁₈ aroyloxy, C₆ to C₁₈ substituted aroyloxy; and all substituents are independently selected from the group that consists of epoxy, hydroxy, C₁ to C₁₈ alkoxy, acyl, acyloxy, alkoxycarbonyl, aryloxycarbonyl, cyano, silyl, halo, and C₁ to C₁₈ dialkylamino.

2. A process for preparing the polymers of claim 1 comprising contacting reactant (i) with one or both of reactants (ii) and (iii) wherein:

(i) is at least one monomer M;

(ii) is at least one nitroxide of Formula (1)

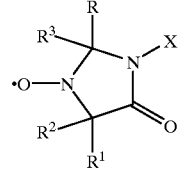

(1)

and a source of free radicals Y•; and (iii) is at least one alkoxyamine selected from the formula

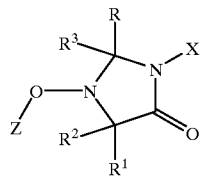

Formula (3)

wherein:
R, $R^1$, $R^2$, $R^3$ are each independently selected from the group consisting of $C_1$ to $C_{18}$ alkyl, substituted $C_1$ to $C_{18}$ alkyl, $C_6$ to $C_{18}$ aryl, $C_6$ to $C_{18}$ substituted aryl; R groups in a geminal position with respect to each other can together form a 4–8 membered ring; and R groups in a cis position with respect to each other can together form a 4–8 membered ring;

X is selected from the group consisting of hydrogen, $C_1$ to $C_{18}$ alkyl, substituted $C_1$ to $C_{18}$ alkyl, $C_6$ to $C_{18}$ aryl, $C_6$ to $C_{18}$ substituted aryl; acyl; X and R can form a 5–8 membered ring; and X and $R^3$ can form a 5–8 membered ring;

M is one or more monomer units selected from the group consisting of styrene, substituted styrene, alkyl acrylate, alkyl methacrylate, substituted alkyl acrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene and butadiene;

Y is a residue derived from a species that initiates free radical polymerization or is selected from the group consisting of $C_1$ to $C_{18}$ alkyl, substituted $C_1$ to $C_{18}$ alkyl, $C_1$ to $C_{18}$ alkoxy, substituted $C_1$ to $C_{18}$ alkoxy, $C_6$ to $C_{18}$ aryl, $C_6$ to $C_{18}$ substituted aryl, $C_6$ to $C_{18}$ aroyloxy, $C_6$ to $C_{18}$ substituted aroyloxy, ($C_1$ to $C_{18}$ alkoxy)carbonyloxy, ($C_6$ to $C_{18}$ aryloxy)carbonyloxy, and sulfate radical anions; all substituents are independently selected from the group that consists of epoxy, hydroxy, $C_1$ to $C_{18}$ alkoxy, acyl, acyloxy, alkoxycarbonyl, aryloxycarbonyl, cyano, silyl, halo, and $C_1$ to $C_{18}$ dialkylamino;

Z is a group having at least one carbon atom and is such that the carbon centered radical Z• is capable of initiating free radical polymerization of the monomer (M); and Y and the reaction conditions are selected so that the $Y(M)_n$—O moiety in the compounds of Formula (2) formed from reactants (i) and (ii) undergo facile homolysis;

Z and the reaction conditions are selected so that the Z—O moiety and the $Z(M)_n$—O moiety formed by reacting (i) and (iii) undergo facile homolysis; and n is an integer of 1 or greater.

* * * * *